US010591463B2

(12) United States Patent
Thompson et al.

(10) Patent No.: US 10,591,463 B2
(45) Date of Patent: Mar. 17, 2020

(54) METHOD OF PREDICTING PHENOTYPIC INSTABILITY IN A CELL

(71) Applicant: Valitacell Limited, County Dublin (IE)

(72) Inventors: Ben Thompson, Sheffield (GB); David James, Sheffield (GB); Jerry Clifford, Tralee (IE)

(73) Assignee: Valitacell Limited, County Dublin (IE)

( * ) Notice: Subject to any disclaimer, the term of this patent is extended or adjusted under 35 U.S.C. 154(b) by 598 days.

(21) Appl. No.: 15/301,319

(22) PCT Filed: Apr. 2, 2015

(86) PCT No.: PCT/EP2015/057392
§ 371 (c)(1),
(2) Date: Sep. 30, 2016

(87) PCT Pub. No.: WO2015/150551
PCT Pub. Date: Oct. 8, 2015

(65) Prior Publication Data
US 2017/0030894 A1    Feb. 2, 2017

(30) Foreign Application Priority Data

Apr. 4, 2014  (EP) ..................................... 14163519

(51) Int. Cl.
*G01N 33/50*       (2006.01)

(52) U.S. Cl.
CPC ....... *G01N 33/502* (2013.01); *G01N 33/5008* (2013.01)

(58) Field of Classification Search
CPC .................................................. G01N 33/502
USPC ........................................................ 702/19
See application file for complete search history.

(56) References Cited

U.S. PATENT DOCUMENTS

| | | | |
|---|---|---|---|
| 5,328,985 A | 7/1994 | Sano et al. | |
| 5,660,991 A | 8/1997 | Lakowicz et al. | |
| 7,427,473 B2 | 9/2008 | Strovel et al. | |
| 8,492,144 B2 | 7/2013 | Dorai et al. | |
| 2001/0051331 A1 | 12/2001 | Nakayama et al. | |
| 2002/0150890 A1 | 10/2002 | Nakayama et al. | |
| 2003/0235813 A1 | 12/2003 | Luyten et al. | |
| 2005/0095655 A1 | 5/2005 | Montero-Julian et al. | |
| 2005/0204418 A1 | 9/2005 | Jung et al. | |
| 2006/0105397 A1 | 5/2006 | Cullum et al. | |
| 2007/0184447 A1 | 8/2007 | Strovel et al. | |
| 2009/0117647 A1 | 5/2009 | Buddhi Srinivasa et al. | |
| 2009/0197243 A1 | 8/2009 | Rieder et al. | |
| 2009/0287320 A1 | 11/2009 | MacGregor et al. | |
| 2010/0152417 A1 | 6/2010 | Taki et al. | |
| 2010/0033036 A1 | 12/2010 | Lambrecht et al. | |
| 2010/0330036 A1 | 12/2010 | Lambrecht et al. | |
| 2011/0143387 A1 | 6/2011 | Patsenker et al. | |
| 2012/0190073 A1 | 7/2012 | Chartrain et al. | |
| 2014/0199728 A1 | 7/2014 | Du et al. | |
| 2016/0139109 A1 | 5/2016 | Thompson et al. | |
| 2017/0017891 A1 | 1/2017 | Thompson et al. | |
| 2017/0160286 A1 | 6/2017 | Thompson et al. | |
| 2018/0282779 A1 | 10/2018 | Clifford et al. | |
| 2019/0011437 A1 | 1/2019 | Clifford et al. | |

FOREIGN PATENT DOCUMENTS

| | | |
|---|---|---|
| CN | 101186880 A | 5/2008 |
| CN | 201569914 U | 9/2010 |
| CN | 102220239 A | 10/2011 |
| EP | 0957365 A1 | 11/1999 |
| JP | 2005337805 A | 12/2005 |
| WO | 96/13722 A1 | 5/1996 |
| WO | 97/23642 A1 | 7/1997 |
| WO | 97/39236 A1 | 10/1997 |
| WO | 97/39326 A2 | 10/1997 |
| WO | WO 01/81895 A2 | 11/2001 |
| WO | WO 02/37102 A2 | 5/2002 |
| WO | WO 2006/135992 A1 | 12/2006 |
| WO | 2008/141317 A1 | 11/2008 |
| WO | 2009/078876 A1 | 6/2009 |
| WO | 2013/144359 A2 | 10/2013 |
| WO | 2014/207166 A1 | 12/2014 |

(Continued)

OTHER PUBLICATIONS

Aoyagi, S., et al. "Development of Fluorescence Change-Based, Reagent-Less Optic Immunosensor," Biosensors and Bioelectronics, 20(8): 1680-1684 (Feb. 2005).

(Continued)

*Primary Examiner* — Jerry Lin

(74) *Attorney, Agent, or Firm* — Hamilton, Brook, Smith & Reynolds, P.C.

(57) ABSTRACT

A method for predicting the phenotypic stability of a cell line comprises the steps of culturing the cell line over an assay period, and generating an environmental response fingerprint for the cell line at a plurality of different time points over the assay period, wherein each environmental response fingerprint is generated by determining the environmental response of the cells in the presence of each of a plurality of chemical cell stressors. The plurality of environmental response fingerprints are compared to detect change in the environmental response fingerprint over the assay period. The level of change in the environmental response fingerprint over the assay period is indicative of the level of predicted phenotypic instability in the cell line. The environmental response may be growth response, productivity response, or another detectable environmental response.

13 Claims, 2 Drawing Sheets

(56) References Cited

FOREIGN PATENT DOCUMENTS

| | | |
|---|---|---|
| WO | 2015/113704 A1 | 8/2015 |
| WO | 2015/150551 A1 | 10/2015 |
| WO | 2016/008671 A1 | 1/2016 |
| WO | 2016/156604 A1 | 10/2016 |
| WO | 2017/103210 A1 | 6/2017 |

OTHER PUBLICATIONS

Carmichael et al., "Chemosensitivity testing of human lung cancer cell lines using the MTT assay," British Journal of Cancer 57 .6 (1988): 540. (Year: 1988).

"Cell Culture Media—Addressing Variability in Dry Powder Mammalian Cell Culture Media," retrieved from the internet: URL:http://drug-dev.com/Main/Back-Issues/CELL-CULTURE-MEDIA-Addressing-Variability-in-Dry-P-598.aspx, retrieved on Jun. 10, 2015, listed posted date: Jun. 10, 2013.

Chen, Min, et al., "A novel multiplexed fluorescence polarisation immunoassay based on a recombinant bi-specific single-chain diabody for simultaneous detection of fluoroquinolones and sulfonamides in milk," Food Additives & Contaminants, Part A, vol. 31(12): 1959-1967 (Nov. 13, 2014).

Curtis, G.D.W., "A Review of Methods for Quality Control of Culture Media," Int. Journal of Food Microbiology, 2: 13-20 (Jan. 1985).

Gao et al., "Powerful and prolonged protection of human retinal pigment epithelial cells, keratinocytes, and mouse leukemia cells against oxidative damage: the indirect antioxidant effects of sulforaphane," Proceedings of the National Academy of Sciences 98.26(2001): 15221-15226 (Year: 2001).

Godoy-Silva, et al., "Physiological Responses of CHO Cells to Repetitive Hydrodynamic Stress," Biotechnology and Bioengineering, vol. 103, No. 6, Aug. 15, 2009, pp. 1103-1117.

International Preliminary Report on Patentability for Int'l Application No. PCT/EP2014/078340, entitled: "A Method of Predicting Relative Fed Batch Production Titer of a Panel of Clonally-Derived Producer Cells," dated May 24, 2016.

International Preliminary Report on Patentability for Int'l Application No. PCT/EP2014/063625, entitled: "A Method of Determining or Predicting a Characteristic of a Cell," dated Dec. 29, 2015.

International Preliminary Report on Patentability for Int'l Application No. PCT/EP2015/057392, entitled: "A Method of Predicting Phenotypic Instability in a Cell," dated Oct. 4, 2016.

International Search Report and the Written Opinion of the International Searching Authority, consisting of 18 pages, for PCT/EP2014/063625, entitled "A Method of Determining or Predicting a Characteristic of a Cell," dated Oct. 24, 2014.

International Search Report and Written Opinion for lnt'l Application No. PCT/EP2016/057283, entitled: "A Method of Determining a Compositional or Functional Characteristic of a Cell Culture Media," dated Jun. 24, 2016.

Gokulrangan, G., et al., "DNA Aptamer-Based Bioanalysis of IgE by Fluorescence Anistropy," Analytical Chemistry, 77(7): 1963-1970 (Apr. 1, 2005).

Restriction Requirement for U.S. Appl. No. 14/900,113, dated Mar. 28, 2018.

Jostock, et al., "Combination of the 2A/Furin Technology with an Animal Component Free Cell Line Development Platform Process," Applied Microbiology and Biotechnology, vol. 87, No. 4, May 12, 2010, pp. 1517-1524.

Lea, W.A., et al., "Fluorescence Polarization Assays in Small Molecule Screening," Expert Opinion on Drug Discovery, 6:(1): 17-32 (Jan. 2011).

Li, B., et al., "Rapid Characterisation and Quality Control of Complex Cell Culture Media Solutions Using Raman Spectroscopy and Chemometrics," Biotechnology and Bioengineering 107(2): 290-301 (2010).

Moerke, N.J., "Fluorescence Polarization (FP) Assays for Monitoring Peptide-Protein or Nucleic Acid-Protein Binding," Current Protocols in Chemical Biology, vol. 1: 1-15 (Dec. 2009).

"NMR-Based Methods Fingerprinting Culture Media," Retrieved from Internet at: http://www.spinnovation-analytical.com/images/stories/press-releases/SPI-JOB-035-article.pdf, Retrieved on: Jun. 10, 2015 (whole document).

Non Final Office Action for U.S. Appl. No. 14/900,113, dated Aug. 8, 2018.

Ryan, P.W. et al., "Prediction of Cell Culture Media Performance Using Fluorescence Spectroscopy," Analytical Chemistry, 82(4): 1311-1317 (Feb. 2010).

Restriction Requirement for U.S. Appl. No. 15/114,359, dated Sep. 10, 2018.

Wang, Z-H., et al., "Analysis of Sulfamethazine by Fluorescence Polarization Immunoassay," Chinese Journal of Analytical Chemistry, 35(6): 819-824 (Jun. 2007).

Yen, Sandi et al., "Treating cell culture media with UV irradiation against adventitious agents: Minimal impact on CHO performance," Biotechnology Progress, 30(5): 1190-1195 (Jul. 2014).

Zhang, S., et al., "Fluorescence Polarisation Immunoassay Based on Monoclonal Antibody for the Detection of Sulphamethazine in Chicken Muscle," International Journal of Food Science and Technology, 42(1): 36-44 (Jan. 1, 2007).

International Search Report and the Written Opinion for PCT/EP2014/078340, entitled "A Method of Predicting Relative Fed Batch Production Titer of a Panel of Clonally-Derived Producer Cells," dated Mar. 23, 2015.

Da Cruz Meleiro, et al., "Non-Linear Multivariable Predictive Control of an Alcoholic Fermentation Process Using Functional Link Networks," Brazilian Archives of Biology and Technology, Instituto De Tecnologia Do Parana, BR, vol. 48, No. Special, Jun. 2005, pp. 7-18.

Dorai, Haimanti, et al., "Combining high-throughput screening of caspase activity with anti-apoptosis genese for development of robust CH0 production cell lines," Biotechnology Progress, 26(5): 1367-1381 (Sep. 2010).

Legmann, et al., "A Strategy for Clone Selection Under Different Production Conditions," Biotechnology Progress, vol. 27(3): 757-765 (May 29, 2011).

Xu, Jianlin, et al., "Galactose can be an inducer for production of therapeutic proteins by auto-induction using BL21 strains," Protein Expression and Purification, 83(1): 30-36 (Jun. 2005).

International Preliminary Report on Patentability for International Application No. PCT/EP2016/057283, entitled "A Method of Determining a Compositional or Functional Characteristic of a Cell Culture Media," dated Oct. 3, 2017.

Gunther, J.C. et al., "Process monitoring and quality variable prediction utilizing PLS in industrial fed-batch cell culture," Journal of Process Control, 19: 914-921 (2009).

Kim, J.Y. et al., "CHO cells in biotechnology for production of recombinant proteins: current state and further potential," Appl. Microbiol. Biotechnol., 93:917-930 (2012).

Non-Final Office Action for U.S. Appl. No. 15/114,359, dated Feb. 25, 2019.

Final Office Action for U.S. Appl. No. 14/900,113, dated Mar. 1, 2019.

International Search Report and Written Opinion dated Jul. 21, 2015 of International Application No. PCT/EP2015/057392, "A Method of Protecting Phenotypic Instability in a Cell", International Filing Date Apr. 2, 2015.

Cudre-Mauroux, C., et al., "Lentivector-Mediated Transfer of BMI-1 and Telomerase in Muscle Satellite Cells Yields a Duchenne Myoblast Cell Line With Long-Term Genotypic and Phenotypic Stability," Human Gene Therapy, 14: 1525-1533 (Nov. 2003).

Gignac, S.M., "Multiparameter Approach in the Identification of Cross-Contaminated Leukemia Cell Lines," Database Medline [Online] US National Library of Medicine, Bethesda, MD, US, XP002730560, Database accession No. NLM8220135, abstract & Leukemia & Lymphoma vol. 10, No. 4-5, pp. 359-368 (1993).

Nakatsu, N., et al., "Evaluation of Action Mechanisms of Toxic Chemicals Using JFCR39, a Panel of Human Cancer Cell Lines, "Molecular Pharmacology, 72: 1171-1180 (2007).

(56) References Cited

OTHER PUBLICATIONS

Schwartz, R., et al., "Heterogeneity of Glycoprotein Synthesis in Human Tumor Cell Lines," Eur. J. Cancer Clin. Oncol., 22(3): 273-281 (1986).
Non-Final Office Action for U.S. Appl. No. 15/562,403, dated May 1, 2019.
Fowler, et al., "Self-Assembled Layer of Thiolated Protein G as an Immunosensor Scaffold," Anal. Chem., 79, (2007), p. 350-354 (Year: 2007).
Li, et al., Cell culture processes for monoclonal antibody production, Landes Bioscience, 2(5), (2010), p. 466-477 (Year: 2010).
Sayoko, et al., Machine translation of JP2005337805 (English Translation of the Disclosure), obtained via Dialog on Jul. 11, 2019 at [https://dialog.proquest.com.professional/japanpatentsft/docview/1390751074/16B46B58CBE203E90EE/2?] (Year: 2005).
Final Office Action for U.S. Appl. No. 15/562,403, entitled "A Method of Determining a Compositional or Functional Characteristic of a Cell Culture Media," dated Nov. 8, 2019.
Non-Final Office Action for U.S. Appl. No. 14/900,113, dated Oct. 21, 2019
Final Office Action for U.S. Appl. No. 15/114,359, entitled "A Method of Predicting Relative Fed Batch Production Titer of a Panel of Clonally-Derived Producer Cells" dated Dec. 11, 2019.
Li, et al., "Cell Culture Processes in Monoclonal Antibodies", Pharmaceutical Sciences Encyclopedia; Drug Discovery, Development and Manufacturing, Edited by Shayne C. Gad (2013); pp. 1-36 (Year 2013).
Notice of Allowance for U.S. Appl. No. 15/562,403, entitled "A Method of Predicting Relative Fed Batch Production Titer of a Panel of Clonally-Derived Producer Cells," dated Jan. 2, 2020.
Notice of Allowance for U.S. Appl. No. 15/562,403, entitled "A Method of Determining A Compositional or Functional Characteristic of a Cell Culture Media," dated Jan. 2, 2020.

METHOD OF PREDICTING PHENOTYPIC INSTABILITY IN A CELL

RELATED APPLICATIONS

This application is the U.S. National Stage of International Application No. PCT/EP2015/057392, filed Apr. 2, 2015, which designates the U.S., published in English, and claims priority under 35 U.S.C. §§ 119 or 365(c) to EP Application No. 14163519.3, filed Apr. 4, 2014. The entire teachings of the above applications are incorporated herein by reference.

INTRODUCTION

The invention relates to a method of predicting phenotypic instability in a cell, typically a mammalian producer cell.

BACKGROUND TO THE INVENTION

From a regulatory point of view the main aspects of stability purely concern the product, namely consistent characteristics of the product (for example consistent glycoforms and more generally, in-vivo activity).

However, from a manufacturing point of view, important aspects of stability are naturally product quality but also consistent growth and productivity of the producing cell line clone. For example, from Lonza™ guidelines, a change of over 30% in product titre over 40 doublings (roughly 10 passages) is deemed an unstable cell line.

Changes in the cell line can be attributed to changes in gene copy number, mRNA copy number and underlying changes to the cell on the whole (i.e. changes to proteome and metabolome). Changes to a cell's genome implies a degree of phenotypic genetic instability, or a "mutator phenotype" (Loeb et al 1999). It is likely that any cell line clone which has become this phenotype will be subject to other linked changes in phenotype.

It is an object of the invention to overcome at least one of the above-referenced problems.

STATEMENTS OF INVENTION

The invention provides a method for predicting the phenotypic stability of a cell line comprising the steps of:
  culturing the cell line over an assay period;
  generating an environmental response fingerprint for the cell line at a plurality of different time points over the assay period, wherein each environmental response fingerprint is generated by determining the environmental response of the cells in the presence of each of a plurality of chemical cell stressors; and
  comparing the plurality of environmental response fingerprints to detect change in the environmental response fingerprint over the assay period, wherein the level of change in the environmental response fingerprint over the assay period is indicative of the level of predicted phenotypic instability in the cell line.

Typically, the step of comparing the plurality of environmental response fingerprints to detect change in the environmental response fingerprint over the assay period comprises the step of detecting a change in the or each chemical cell stressor specific environmental response.

Suitably, the environmental response is a growth response.

Preferably, the plurality of different time points span one or more passages over the assay period.

Typically, the environmental response fingerprint is generated at three or more time points during the assay period.

Suitably, the environmental response fingerprint is generated at four or more time points during the assay period.

Generally, each environmental response fingerprint is generated by determining the environmental response of the cells in the presence of each of at least three different chemical cell stressors.

Preferably, each environmental response fingerprint is generated by determining the environmental response of the cells in the presence of each of at least five different chemical cell stressors.

Suitably, the chemical cell stressors are selected from amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin.

Generally, the cell line is a mammalian producer cell line.

Typically, change in the environmental response fingerprint over the assay period is determined means of a mathematical model, suitably a mathematical model generated using one or more environmental response fingerprints of cells having known phenotypic stability or instability, or both. Typically, the mathematical model employs a means selected from Euclidian distance, mahalanobis distance, LDA distance, PCA distance.

The invention also provides a system for identifying a cell, the system comprising:
  a device comprising a plurality of reaction chambers;
  a plurality of chemical cell stressors disposed individually within the reaction chambers;
  a determination system for determining an environmental response of the cell in the presence of each of the plurality of chemical cell stressors;
  a storage system for storing a plurality of environmental response fingerprints, each corresponding to the plurality of environmental responses of the cell;
  a comparison system configured to compare at least some of the plurality of environmental response fingerprint to detect change in the environmental response fingerprints; and
  a display system for displaying an output of the comparison step.

Suitably, the environmental response fingerprint is a growth response fingerprint.

Typically, the device is a microtitre plate.

Suitably, the comparison system comprises a computational model configured to input an environmental response fingerprints from a cell at a plurality of different time points over an assay period, compare the growth response fingerprints to detect change in the fingerprints, and output a content based in part on the change in the fingerprints.

DETAILED DESCRIPTION OF THE INVENTION

In this specification, the term "cell" refers to any cell type, including prokaryotic or eukaryotic cells. Suitably, the cell is a eukaryotic cell, ideally a mammalian cell. Typically, the cell is a producer cell, preferably a mammalian producer cell. The cell may be clonally-derived or non-clonal. In a preferred embodiment, the cell is a clone from a panel of clonal cells, derived from a single parental cell population or derived from different transfected cells. The cell may also be from a distinct cell line, for example a genetically modified cell (i.e. cells with "knock-out" or "knock-in" mutations. The cell line may also be derived by directed evolution, by selection of cells which have adapted to a specific environment of interest. The term "panel of distinct cells" should be understood to mean a panel of cells that are different from each other. For example, the panel of cell may comprise a panel of clones that are all derived from a single parental cell population. Alternatively, the panel of cells may comprise cells of independent clonal origin, for example cells carrying different transgenes or different mutations, of the panel of cells may comprise non-clonal cells. The cell line may also be derived by directed evolution, by selection of cells which have adapted to a specific environment of interest. The panel of cells may also comprise cells of different cell type, for example different cell lines, different strains of bacteria or fungi, cells of the same cell type but at a different stage of development, and cells of the same cell type that differ genetically, for example cells of the same type or origin or cells derived from the same parental cell population that carry different transgenes.

In this specification, the term "panel of clonal cells" should be understood to mean a panel of clonal cell populations derived from a single cell line, and comprising from 2 to 500 or more clonal cell populations. Methods for generating panels of clonal cells are well known to a person skilled in the art, and described in Production of recombinant protein therapeutics in cultivated mammalian cells (2004), Wurm, Florian M, New York, N.Y., *Nature Biotechnology* 22 (2004), S. 1393-1398. Typically, the panel of clonal cell populations include from 10-500, 20-500, 30-500, 40-500, 50-500, 60-500, 70-500, 80-500, 90-500 or 100-500 clonal cell populations. Typically, the panel of clonal cell populations include from 100-500, 100-400, 150-400, 150-350 clonal cell populations.

The invention involves incubating a cell with a plurality of cell stressor molecules. This means that the cell is incubated with each of the cell stressor molecules individually, to obtain a growth response of the cell in the presence of each cell stressor molecule. Incubation of the cell with the cell stressor molecule may be performed in any suitable reaction vessel, for example in the wells of a microtitre plate. Typically, the assay involves mixing a cell sample with a chemical cell stressor, and incubating the mixture from 1 to 4 days, and assaying the level of growth of the cells. Suitably, the cell sample is provided at a concentration of from 0.1 to $1.0 \times 10^6$ cells per ml of mixture. Typically, the cell stressor is provided at a concentration of 0.5 to 2×IC50, ideally about 1×IC50. Suitably, the growth of each clone is assayed after a period of incubation of less than 5 days. Ideally, the growth of each clone is assayed after a period of incubation of between 1-4 days, and ideally after 2 and 3 days. Preferably, the growth of each clone is assayed simultaneously.

The term "cell stressor molecule" or "cell stressor" should be understood to mean a molecule or compound that causes a reduction in cell growth via one or more of multiple cellular pathways. Typically, the plurality of chemical cell stressors are selected from the group consisting of amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin. Typically, the plurality of chemical cell stressors include stressors selected from at least 4, 5, 6 or 7 of the groups consisting of amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin.

In this specification, the term "plurality" as applied to cell stressor molecules should be understood to mean at least three different cell stressor molecules. Typically, the term refers to at least 4, 5, 6, 7, 8, 9, 10, 11, 12, 13, 14, 15, 16, 17, 18, 19 or 20 different cell stressor molecules. Thus, the method of the invention may be performed by employing as few as three distinct cell stressor molecules to generate the cell-specific growth response fingerprint, for example: $CoCl_2$, NAV and MSB; Cadm, MSB and 2DG; Cadm, dphe, MeIAB; dphe, MeIAB, Cadm; Dphe, Cadm, 2dg; Dphe, sodium lactate, 2dg; Dphe, NaOx, citric acid; MeIAB, Cad, 2dg.

The term "environmental response" refers to a measurable response of the cell when exposed to a cell stressor molecule, for example growth response, production response (for example monoclonal antibody titre), or glycosylation response. Typically, the environmental response is a normalised environmental response, which is determined by measuring the environmental response of the cell in the presence and absence of the cell stressor molecule and determining the difference in environmental response due to the presence of the cell stressor molecule.

The term "growth response" refers to the growth of the cell in the presence of a cell stressor molecule. Typically, the growth response is a normalised growth response, which is determined by measuring the growth of in the presence and absence of the cell stressor molecule and determining the difference in growth response due to the presence of the cell stressor molecule. Growth of cells may be determined using any technique known in the art. In one embodiment, a dye is added to the incubation mixture and a signal emitted by the dye is monitored over time and correlated with growth. For example, a fluorescent or phosphorescent dye may be employed. Examples of suitable dyes are redox dyes, such as Presto Blue®. (Invitrogen, Paisley, UK).

The term "phenotypic instability" should be understood to mean instability of one or more phenotypic characteristics of a cell, for example growth, productivity, and recombinant protein product characteristics.

The term "environmental response fingerprint" refers to a plurality of environmental responses for a specific cell obtained by reacting the cell with a plurality of cell stressor molecules individually. The fingerprint may be embodied as a plurality of environmental response values, or may be embodied in the form of a graph or any other type of visual presentation such as a pattern. Change in fingerprint over time may be determined by monitoring environmental change in the or each chemical microenvironment.

The term "growth response fingerprint" refers to a plurality of growth responses for a specific cell obtained by reacting the cell with a plurality of cell stressor molecules individually. The fingerprint may be embodied as a plurality of growth response values, or may be embodied in the form of a graph or any other type of visual presentation such as a pattern.

The term "assay period" refers to a period of time during which the cells to be tested are cultured. Typically, the assay period spans at least 5, 6, 7, 8, 9, 10, 11, 12, 13, 14, 15, 16, 17, 18, 19 or 20 passages of the cells.

The term "plurality of different time points" refers to at least 2, 3, 4, 5, 6, 7, 8, 9, or 10 different time points. Generally each time point is separated by at least 1, 2 or 3 passages.

One aspect of the invention involves comparing environmental response fingerprints (i.e. growth response fingerprint) for a cell over the course of an assay period to detect change in the environmental response fingerprint, which is then correlated with the stability or instability of the cell. The term "change" as applied to an environmental response fingerprint refers to at least one difference in environmental response fingerprint that occurs during the assay period. Various methods may be employed to detect changes in environmental response fingerprints over time including mathematical modelling, pattern recognition, or by visual inspection. For example, the environmental responses for a cell at time points A, B and C may be plotted against cell stressors to provide graphs representing the environmental response fingerprint for the cell at time points A, B and C. The environmental response fingerprints may be compared visually to identify changes in the fingerprint over time. Generally, the greater the change in the fingerprint over the assay period, the more unstable the cell. For example, from Lonza™ guidelines, a change of over 30% in product titre over 40 doublings (roughly 10 passages) is deemed an unstable cell line. It is possible using the method of the invention to quantitatively determine the level of change in growth response fingerprint that correlates with an unstable cell line according to the Lonza definition, and thereby use the method of the invention to identify unstable cell lines. In a preferred embodiment, the comparison step may be performed by mathematical modelling, typically using a mathematical model generated using environmental response fingerprints (or chemical specific environmental response) from cells have known phenotypic stability and/or instability, for example cell lines that have a predetermined stability and predetermined instability. The modelling approach may employ 'Linear discriminant analysis' and 'nearest neighbour elucidian distance minimisation', using a subset of the chemical growth responses. Thus, in one embodiment, the method involves the steps of inputting an environmental response fingerprint for a test cell line into a computational model, in which the computational model is generated from environmental response fingerprints obtained from a calibration set of cell lines with known phenotypic stability, wherein the computational model is configured to output the predicted stability for the cell line. The environmental response fingerprint may be one or more chemical-specific change in environmental responses ($\Delta$CE).

The invention also provides a system or kit for identifying a cell. The system or kit typically comprises a device having a plurality of reaction chambers. Preferably, the device is a microtitre plate, typically a microtitre plate having at least 12, 24, 48, or 96 wells.

The system or kit typically comprises a plurality of cell stressor molecules. Preferably, the cell stressor molecules are disposed individually within the wells of the microtitre plate, and are preferably adhered to the wells of the microtitre plate.

The system or kit comprises a determination system for determining the environmental (i.e. growth) response of the cell in the presence of each of the plurality of chemical cell stressors. Typically, the determination system comprises a microtitre plate reader configured to detect growth of cells in the wells of the microtitre plate. Suitable microtitre plate readers are commercially available, and are sold by the company BMG. The determination system typically has computer executable instructions to provide e.g., growth response data in computer readable form.

The system or kit also comprises a storage system and a comparison system (for comparing growth response fingerprint data for cells at different time points). These functional modules can be executed on one, or multiple, computers, or by using one, or multiple, computer networks. The determination system has computer executable instructions to provide e.g., sequence information in computer readable form.

The information determined in the determination system can be read by the storage system. As used herein the "storage system" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage system is adapted or configured for having recorded thereon growth response information and growth response fingerprint information. Such information may be provided in digital form that can be transmitted and read electronically, e.g., via the Internet, on diskette, via USB (universal serial bus) or via any other suitable mode of communication.

The storage system may have reference environmental (i.e. growth) response fingerprint information stored thereon. As used herein, "stored" refers to a process for encoding information on the storage device. In one embodiment the reference data stored in the storage device to be read by the comparison module is compared, e.g., comparison of a query cell-specific growth response fingerprint with a set or panel of reference growth response fingerprints.

The "comparison system" can use a variety of available software programs and formats for the comparison operative to compare environmental response fingerprints from a cell at different time points over an assay period to detect change in the environmental (i.e. growth) response fingerprints. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the genotype of the sample. Preferably, the comparison system employs a computational model for comparison purposes.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module typically provides a computer readable comparison result that can be processed in computer readable form by predefined criteria, or criteria defined by a user, to provide a content based in part on the comparison result that may be stored and output as requested by a user using a display system.

In one embodiment of the invention, the content based on the comparison result is displayed on a computer monitor. In one embodiment of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

DETAILED DESCRIPTION OF THE INVENTION

Experimental

Figure 1:
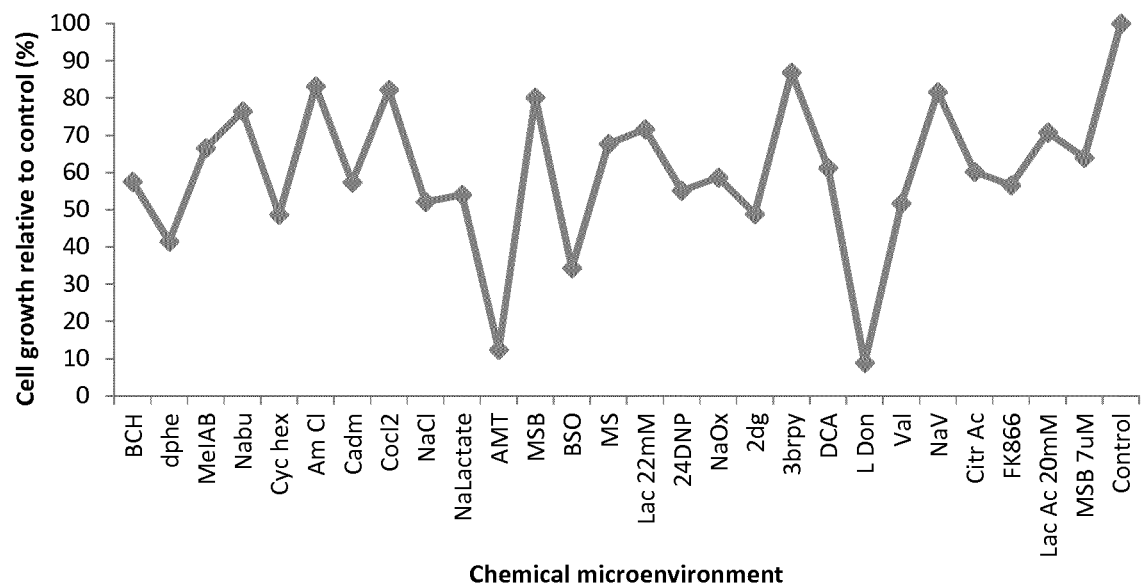
FIG. 1: An example of a chemical growth fingerprint from a clone. Cells were grown for 72 hours in the presence or absence of a chemical of interest in a 96 well plate. Relative levels of cell growth were assayed using the "Presto-Blue" method as described above.

Small Scale Determination of Cell Growth:
Assaying cell growth in 96 well plates: "Presto Blue" (Invitrogen, Paisley, UK) was mixed 1:1 with CD-CHO media and 20 ul of this was added to each well. The plate was machine shaken and subsequently incubated for 30 minutes at 37 C in a static humidified incubator. After incubation the fluorescence of the wells was measured (excitation 535 nm emission 620 nm) using a fluoroskan ascent (Thermo-Fisher, Loughborough, UK) plate reader. It has been demonstrated prior that fluorescence is linearly correlated with viable cell density in the wells.

Preparation of the Chemical Test Plate:
Method: The plurality of cell stressor molecules employed were:
2-aminobicyclo-(2,2,1)heptane-carboxylic acid (BCH)
D-phenylalanine-(D-Phe)
α-(methylamino)isobutyric acid (MeAIB)
Sodium Butyrate (NaBu)
Cycloheximide
Ammonium chloride
Cadmium acetate hexhydrate
Cobalt chloride ($CoCl_2$)
Sodium Chloride (NaCl)
Sodium lactate (NaLac)
Aminotriazole (AMT)
Menadione Sodium Bisulphite (MSB)
Buthionine Sulfoximine (BSO)
Mercaptosuccinic Acid (MS)
2,4,Dinitrophenol (24DNP)
Sodium Oxamate
2-deoxyglucose (2dg)
3-bromopyruvate (3-BrPA)
Dichloroacetate (DCA)
6-diazo-5-oxo-1-norleucine (1-don)
Valproic acid (Val)
Sodium Orthovandate (NaV)
Citric acid
FK866
Lactic acid Using an 'in house' parental cell line, inhibitory dose 50 (IC50) concentrations of the above chemicals were identified through growth studies. Here IC50 is defined as the concentration of the chemical, in question, which inhibits normal cell growth by 50% over a 3 day period. Once IC50s were established, 96 well plates were set up containing the above selection of chemicals at the IC50 concentration and including control wells which contained only cell growth media.

A Method of Predicting Stability:
Starting with an early passage, before any instability has become apparent, fingerprints are taken over a number of passages. The first fingerprint taken is henceforth referred to as the "reference fingerprint". The metrics of interest here are not the growth responses in the microenvironments but the change in growth responses relative to the reference fingerprint.

Thus for each fingerprint taken after the reference fingerprint, a "change in chemical specific growth response" (ΔCE) is calculated for each microenvironment. It is likely that this is the most informative metric pertaining to stability. These ΔCEs for each micro-environment are used as the parameters in a predictive model to give a binary output of stable or unstable.

This model employed to predict stability is selected from a variety of models. One suitable example is a "linear discriminant model" (LDA) model where linear combinations of the ΔCEs are used to maximally separate the stable cell lines from unstable cell lines. Alternatively, the model is be a logistic regression model or is based on simple Euclidian distance or distance in another "space" such as PCA or LDA space. Additionally techniques such as "support vector machines" could be employed.

For the evaluation of a new cell line of interest, a reference fingerprint and a number of subsequent fingerprints are taken to generate the ΔCE fingerprints. These ΔCEs from subsequent fingerprints are used in a modeling approach to predict "stable or unstable" or alternatively some other continuous metric of stability such as "degree of instability". In one embodiment, aspects of stability are predicted as soon as the first passage after the "reference fingerprint".

In one embodiment a "calibration set" of cell lines is not required and stability is consistently predicted by looking for a change from the reference fingerprint over time, for example by simple distance from the reference fingerprint or any modeling, pattern recognition or "by eye" methods.

Example

Five stable and four unstable production CHO cell lines were acquired. These were obtained frozen at early, middle and late generation stages of culture. Here unstable is defined as a drop greater than 30% max product titre by the late generation period.

Chemical fingerprints for each cell line at each different time point were obtained by growth in the chemical screening plates for a period of 3 days prior to measuring the growth and titre in the presence of the above mentioned plurality of chemicals. The measured parameter of interest here was the change in chemical responses over the time period, i.e. early, middle and late.

Figure 2:
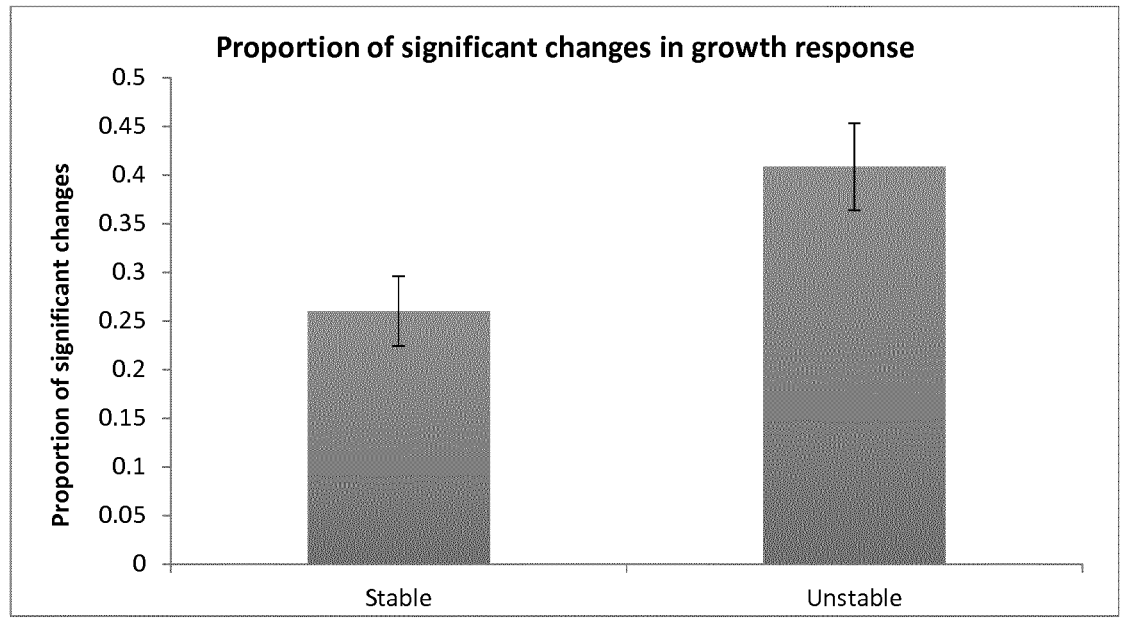
FIG. 2: Proportion of significant changes in growth response between early and late generation cultures. Error bars represent standard deviation of the proportions.

It was observed that frequency of "significant" changes in chemical growth responses was significantly higher for unstable clones than for stable clones between early and late stage culture (FIG. 2). Therefore a likelihood of stability can be obtained by measuring the frequency of significant changes in chemical responses over an appropriate time course. Here a significant change in growth response is defined as a change of more than two standard deviations of the estimated plate to plate standard deviation for a specific chemical growth response. FIG. 2 shows the proportion of chemical changes for unstable clones was 0.41 whereas the proportion of changes for the stable clones was 0.26.

Figure 3:
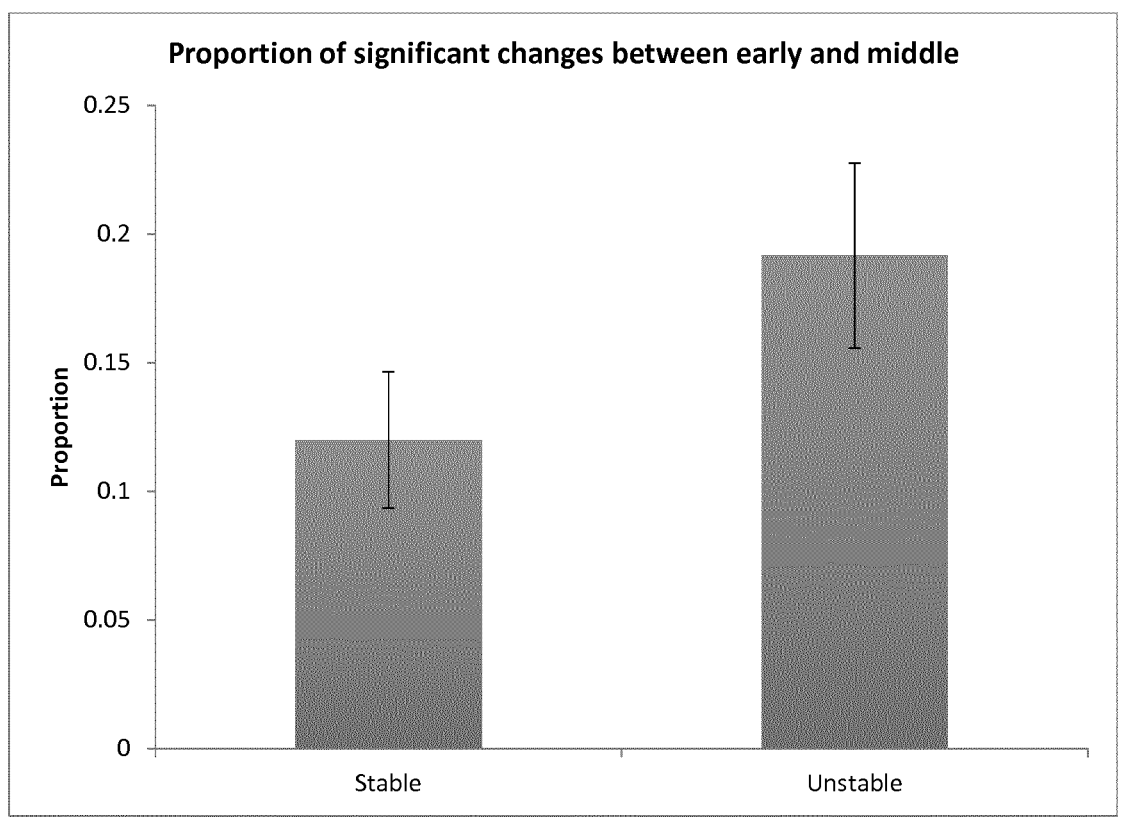
FIG. 3: Proportion of significant changes in growth response between early and middle generation cultures. Error bars represent standard deviation of the proportions.

This effect was also observed between early and middle generation cultures although to a lesser extent (FIG. 3). Again, this demonstrates how change in chemical growth response over a time period can be used as a marker of instability and help screen which clones to take forward into long term growth studies, i.e. clones can be assigned a probability of instability from this. For example, given a number of clones with equally desirable attributes, the present invention allows screening of these clones to determine which to take forward to the next stage of stability studies, saving time and resources.

Conversely, the invention also enables the identification of clones at the early stage which are less desirable in standard attributes such as titre, but are identified as highly likely to be stable from observing low changes in chemical fingerprints. These can be taken forward and potentially chosen over clones, which at an early stage perform well but experience a drop in titre in longer term studies.

The invention is not limited to the embodiment hereinbefore described which may be varied in construction and detail without departing from the spirit of the invention.

The invention claimed is:

1. A computer-implemented method for predicting phenotypic stability of a cell line, the method comprising:
    generating a plurality of environmental response fingerprints by generating an environmental response fingerprint for the cell line at a plurality of different time points in a cell culture assay over an assay period, wherein each environmental response fingerprint is generated based on incubation data obtained from each of the plurality of different time points following simultaneous incubation of the cell line for the assay period in a presence of each of three chemical cell stressors, wherein the cell line is incubated with a single chemical cell stressor of the three chemical cell stressors;
    detecting a change in the environmental response fingerprint over the assay period by comparing the plurality of environmental response fingerprints of the cell line generated in the presence of each of the three chemical cell stressors to an environmental response of the cell line incubated in an absence of the three chemical cell stressors, the environmental response of the cells in the absence of the three chemical cell stressors generating a reference environmental response fingerprint;
    predicting the phenotypic stability of the cell line by applying a computational model generated using one or more environmental response fingerprints of the cell line generated in the presence of each of the three chemical cell stressors and from the reference environmental response fingerprint generated in the absence of the three chemical cell stressors having known phenotypic stability or instability, or both; and
    outputting, from the computational model, a representation of a level of change in the environmental response fingerprint over the assay period in the presence of each of the three chemical cell stressors as compared to the environmental response fingerprint over the assay period in the absence of each of the three chemical cell stressors, thereby providing an indication of a level of predicted phenotypic instability in the cell line.

2. A method as claimed in claim 1, wherein the environmental response is a growth response, production response, or glycosylation response.

3. A method as claimed in claim 1, wherein the plurality of different time points span one or more passage over the assay period.

4. A method as claimed in claim 1, wherein the environmental response fingerprint is generated at three or more time points during the assay period.

5. A method as claimed in claim 1, wherein the environmental response fingerprint is generated at four or more time points during the assay period.

6. A method as claimed in claim 1, wherein each environmental response fingerprint is generated by determining the environmental response of the cells in the presence of each of at least five different chemical cell stressors.

7. A method as claimed in claim 1, wherein the chemical cell stressors are selected from amino acid transport inhibitors, cell cycle inhibitors, a source of carbon, a source of osmotic stress, a source of oxidative stress, an inducer of apoptosis, metabolic effectors, a pH modifier, an inhibitor of glycolysis, and a toxin.

8. A method as claimed in claim 1, wherein the cell line is a mammalian producer cell line.

9. A method as claimed in claim 1, wherein change in the environmental response fingerprint over the assay period is determined by means selected from Euclidian distance, mahalanobis distance, LDA distance, PCA distance.

10. A method as claimed in claim 1, wherein each of the at least three chemical cell stressors is provided at a concentration of 0.5 to 2×IC50.

11. A system for identifying a cell, the system comprising:
    a device including a plurality of reaction chambers;
    at least three chemical cell stressors disposed individually within the plurality of reaction chambers;

a determination system configured to determine an environmental response of the cell in a presence of each of the at least three chemical cell stressors to produce a plurality of environmental responses of the cell;

a storage system configured to store a plurality of environmental response fingerprints, each corresponding to a respective environmental response of the plurality of environmental responses of the cell;

a comparison system configured to compare at least some of the plurality of environmental response fingerprints stored, in the storage system, to detect change in the plurality of environmental response fingerprints; and a display system configured to display an output of content from the comparison system, wherein the comparison system includes a computational model configured to input environmental response fingerprints from a cell at a plurality of different time points over an assay period, compare the environmental response fingerprints to detect change in the environmental response fingerprints, and output the content based in part on the change detected in the environmental response fingerprints.

12. A system as claimed in claim 11, wherein the environmental response fingerprint is a growth response fingerprint, a production response fingerprint, or a glycosylation response fingerprint.

13. A system as claimed in claim 11, wherein the device is a microtiter plate.

* * * * *